(12) United States Patent
Yik et al.

(10) Patent No.: US 12,115,295 B2
(45) Date of Patent: Oct. 15, 2024

(54) HEMODIALYSIS SYSTEM INCLUDING ULTRAVIOLET CHAMBER(S)

(71) Applicant: Fresenius Medical Care Holdings, Inc., Waltham, MA (US)

(72) Inventors: Kelly Yik, Waltham, MA (US); Daniel Schmidt, Waltham, MA (US); Aiyuan Wang, Waltham, MA (US); Deryu Chen, Waltham, MA (US); Christopher McCormick, Waltham, MA (US); Evan Zaro, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 443 days.

(21) Appl. No.: 17/555,630

(22) Filed: Dec. 20, 2021

(65) Prior Publication Data

US 2023/0191010 A1    Jun. 22, 2023

(51) Int. Cl.
*A61M 1/16* (2006.01)
*A61L 2/00* (2006.01)
*A61L 2/26* (2006.01)

(52) U.S. Cl.
CPC .......... *A61M 1/168* (2013.01); *A61L 2/0047* (2013.01); *A61L 2/26* (2013.01); *A61L 2202/11* (2013.01);
(Continued)

(58) Field of Classification Search
CPC .............. A61M 1/168; A61M 2205/11; A61M 2205/3306; A61M 2205/3368;
(Continued)

(56) References Cited

U.S. PATENT DOCUMENTS 4,412,834 A   11/1983   Kulin et al.
4,469,835 A    9/1984   Laurin
(Continued)

FOREIGN PATENT DOCUMENTS

DE   29809867 U1   9/1998
DE   20217081 U1   8/2003
(Continued)

OTHER PUBLICATIONS

Machine-generated English translation of WO 99/62573, generated on May 2, 2024.*
(Continued)

*Primary Examiner* — Fred Prince
(74) *Attorney, Agent, or Firm* — KDW Firm PLLC

(57) ABSTRACT

A hemodialysis system including one or more ultraviolet chambers is disclosed. The hemodialysis system including a dialyzer arranged and configured to filter a patient's blood, a hemodialysis machine arranged and configured to pump, move, or the like dialysate through the dialyzer, the hemodialysis machine including an outlet valve and an outlet fluid flow path to pump or move dialysate from the hemodialysis machine to the dialyzer, and an inlet valve and an inlet fluid flow path to pump or receive dialysate from the dialyzer, and one or more ultraviolet chambers arranged and configured to kill bacteria, viruses, or a combination thereof. Thus arranged, by incorporating one or more ultraviolet chambers in strategic areas of the system, the ultraviolet chambers may eliminate, or at least greatly reduce, the possibility of cross-contamination in, for example, the dialysate, and thus eliminate the need for disinfecting the system between treatments.

11 Claims, 4 Drawing Sheets

FIG. 1

(52) U.S. Cl.
CPC ..... *A61L 2202/122* (2013.01); *A61L 2202/14* (2013.01); *A61L 2202/21* (2013.01); *A61L 2202/22* (2013.01); *A61L 2202/24* (2013.01); *A61M 2205/11* (2013.01); *A61M 2205/3306* (2013.01); *A61M 2205/3368* (2013.01); *A61M 2206/12* (2013.01)

(58) Field of Classification Search
CPC .... A61M 2206/12; A61L 2/0047; A61L 2/26; A61L 2202/11; A61L 2202/122; A61L 2202/14; A61L 2202/21; A61L 2202/22; A61L 2202/24
USPC ..................................... 210/647, 646, 748.11
See application file for complete search history.

(56) References Cited

U.S. PATENT DOCUMENTS

| | | | |
|---|---|---|---|
| 4,475,900 | A | 10/1984 | Popovich et al. |
| 4,774,415 | A | 9/1988 | Biegel et al. |
| 8,197,087 | B2 | 6/2012 | Sobue et al. |
| 8,671,996 | B2 | 3/2014 | Weilhoefer et al. |
| 8,858,792 | B2 | 10/2014 | Ding et al. |
| 2006/0270960 | A1* | 11/2006 | Karp .................. A61M 1/3681 604/6.08 |
| 2007/0176117 | A1 | 8/2007 | Redmond et al. |
| 2009/0012459 | A1 | 1/2009 | Sobue et al. |
| 2010/0051552 | A1 | 3/2010 | Rohde et al. |
| 2010/0072399 | A1 | 3/2010 | Street et al. |
| 2010/0324505 | A1 | 12/2010 | Levenson et al. |
| 2012/0116294 | A1 | 5/2012 | Boenig et al. |
| 2013/0303996 | A1 | 11/2013 | Rasooly et al. |
| 2014/0276373 | A1 | 9/2014 | Minkus |
| 2014/0334974 | A1 | 11/2014 | Rasooly et al. |
| 2015/0165185 | A1 | 6/2015 | Cohen et al. |
| 2016/0082138 | A1 | 3/2016 | Kermode et al. |
| 2016/0271312 | A1 | 9/2016 | Ance et al. |
| 2016/0354503 | A1 | 12/2016 | Hutchens et al. |
| 2017/0072077 | A1 | 3/2017 | Baker et al. |
| 2017/0182305 | A1 | 6/2017 | Kermode et al. |
| 2018/0071445 | A1 | 3/2018 | Suzuki |
| 2019/0224352 | A1 | 7/2019 | Rasooly et al. |
| 2019/0247559 | A1 | 8/2019 | Mochizuki |
| 2020/0030515 | A1 | 1/2020 | Merchant et al. |
| 2020/0188543 | A1 | 6/2020 | Etter et al. |
| 2021/0128807 | A1* | 5/2021 | Poppe .................. A61M 1/1696 |

FOREIGN PATENT DOCUMENTS

| | | | | |
|---|---|---|---|---|
| JP | 2016087071 | A * | 5/2016 | |
| JP | 2017185218 | A | 10/2017 | |
| WO | WO-9962573 | A1 * | 12/1999 | .......... A61M 1/1674 |
| WO | WO-0238191 | A2 * | 5/2002 | ............... A23L 3/28 |
| WO | WO-03105926 | A1 * | 12/2003 | .......... A61M 1/3681 |
| WO | 2022022893 | A1 | 2/2022 | |

OTHER PUBLICATIONS

Machine-generated Enlgish translation of JP 2016-87071, generated on Aug. 27, 2024.*

International Search Report and Written Opinion for the International Patent Application No. PCT/US2022/049892, mailed Feb. 10, 2023, 16 pages.

* cited by examiner

HEMODIALYSIS SYSTEM INCLUDING ULTRAVIOLET CHAMBER(S)

FIELD OF THE DISCLOSURE

The present disclosure generally relates to dialysis machines and systems, and more particularly to a hemodialysis system including one or more ultraviolet chambers (UVC) to disinfect the hemodialysis machine and/or system.

BACKGROUND

Dialysis machines are known for use in the treatment of renal disease. The two principal dialysis methods are hemodialysis (HD) and peritoneal dialysis (PD). As will be readily appreciated by one of ordinary skill in the art, a hemodialysis system is arranged and configured to, inter alia, pump a patient's blood through a dialyzer. In addition, the hemodialysis system includes a HD machine and one or more containers containing a fluid (e.g., a dialysate), which during use is also pumped through the dialyzer of the HD system simultaneously with the patient's blood. A semi-permeable membrane in the dialyzer separates the blood from the dialysate within the dialyzer and allows diffusion and osmosis exchanges to take place between the dialysate and the blood. Thus arranged, in use, the patient's blood is cleaned or filtered.

One disadvantage of hemodialysis systems is that the system may become contaminated with one or more blood viruses such as, but not limited to, influenza, Hepatitis, HIV, etc. As a result, the system must be regularly cleaned to avoid cross-contamination. Generally speaking, current systems require pumping or flowing hot water and/or chemicals through the system. This can be a very time-consuming process and thus, generally speaking, occurs at the end of the day.

It would be beneficial to provide a system where disinfecting the system can occur during the treatment or immediately thereafter to maintain the safety of the system while minimizing downtime of the system (e.g., by providing disinfection during the treatment, disinfecting post-treatment is rendered unnecessary). It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a hemodialysis system is disclosed. In one embodiment, the hemodialysis system includes a dialyzer arranged and configured to filter a patient's blood, a hemodialysis machine arranged and configured to move dialysate through the dialyzer, the hemodialysis machine including an outlet valve and an outlet fluid flow path to move dialysate from the hemodialysis machine to the dialyzer, and an inlet valve and an inlet fluid flow path to receive dialysate from the dialyzer, and one or more ultraviolet chambers arranged and configured to kill bacteria, viruses, or a combination thereof, wherein the one or more ultraviolet chambers include a first ultraviolet chamber positioned in the inlet fluid flow path between the dialyzer and the inlet valve to kill any bacteria, viruses, or combination thereof in the dialysate prior to the dialysate entering the dialysis machine.

In one embodiment, the one or more ultraviolet chambers eliminate a need for disinfecting the dialysis machine between patients.

In one embodiment, the one or more ultraviolet chambers further comprises a second ultraviolet chamber positioned in the outlet fluid flow path between the outlet valve and the dialyzer to kill any bacteria, viruses, or combination thereof in the dialysate prior to entering the dialyzer to kill any bacteria, viruses, or combination thereof, prior to interacting with the patient's blood in the dialyzer.

In one embodiment, the one or more ultraviolet chambers further comprises a third ultraviolet chamber positioned within a substitution fluid path arranged and configured to pump a fluid into a patient's body.

In one embodiment, the dialyzer is arranged and configured to receive and pass therethrough the patient's blood.

In one embodiment, each of the one or more ultraviolet chambers include an inlet for receiving dialysate, an outlet for exiting dialysate, and a fluid flow path extending between the inlet and the outlet, wherein the fluid flow path is arranged and configured to move the dialysate through a spiral trajectory about a longitudinal axis of the chamber.

In one embodiment, ach of the one or more ultraviolet chambers include a plurality of ultraviolets light-emitting diodes (LEDs) arranged and configured to emit ultraviolet light.

In one embodiment, each of the one or more ultraviolet chambers includes an internal chamber extending between first and second ends of the ultraviolet chamber, the internal chamber arranged and configured to house the plurality of ultraviolets light-emitting diodes (LEDs) therein.

In one embodiment, each of the one or more ultraviolet chambers include a photodetector sensor arranged and configured to detect an intensity of the plurality of ultraviolets light-emitting diodes (LEDs) and a temperature sensor arranged and configured to measure a temperature of the dialysate.

In one embodiment, a hemodialysis system is disclosed. In one embodiment, the hemodialysis system includes a dialyzer arranged and configured to filter a patient's blood, a hemodialysis machine arranged and configured to move dialysate through the dialyzer, the hemodialysis machine including an outlet valve and an outlet fluid flow path to move dialysate from the hemodialysis machine to the dialyzer, and an inlet valve and an inlet fluid flow path to receive dialysate from the dialyzer, and one or more ultraviolet chambers arranged and configured to kill bacteria, viruses, or a combination thereof. The one or more ultraviolet chambers include a first ultraviolet chamber positioned in the inlet fluid flow path between the dialyzer and the inlet valve to kill any bacteria, viruses, or combination thereof in the dialysate prior to the dialysate entering the dialysis machine and a second ultraviolet chamber positioned in the outlet fluid flow path between the outlet valve and the dialyzer to kill any bacteria, viruses, or combination thereof in the dialysate prior to entering the dialyzer to kill any bacteria, viruses, or combination thereof, prior to interacting with the patient's blood in the dialyzer.

In one embodiment, the one or more ultraviolet chambers eliminate a need for disinfecting the dialysis machine between patients.

In one embodiment, each of the one or more ultraviolet chambers include an inlet for receiving dialysate, an outlet for exiting dialysate, and a fluid flow path extending between the inlet and the outlet, wherein the fluid flow path is arranged and configured to move the dialysate through a spiral trajectory about a longitudinal axis of the chamber.

In one embodiment, each of the one or more ultraviolet chambers include a plurality of ultraviolets light-emitting diodes (LEDs) arranged and configured to emit ultraviolet light.

In one embodiment, each of the one or more ultraviolet chambers includes an internal chamber extending between first and second ends of the ultraviolet chamber, the internal chamber arranged and configured to house the plurality of ultraviolets light-emitting diodes (LEDs) therein.

In one embodiment, each of the one or more ultraviolet chambers include a photodetector sensor arranged and configured to detect an intensity of the plurality of ultraviolets light-emitting diodes (LEDs) and a temperature sensor arranged and configured to measure a temperature of the dialysate.

In one embodiment, an ultraviolet chamber arranged and configured to be used in a hemodialysis system is disclosed. The ultraviolet chamber includes an inlet for receiving dialysate, an outlet for exiting dialysate, and a fluid flow path extending between the inlet and the outlet, wherein the fluid flow path is arranged and configured to move the dialysate through a spiral trajectory about a longitudinal axis of the chamber.

In one embodiment, the ultraviolet chamber further includes a plurality of ultraviolet light-emitting diodes (LEDs) arranged and configured to emit ultraviolet light.

In one embodiment, the ultraviolet chamber further includes an internal chamber extending between first and second ends of the ultraviolet chamber, the internal chamber arranged and configured to house the plurality of ultraviolets light-emitting diodes (LEDs) therein.

In one embodiment, the ultraviolet chamber further includes a photodetector sensor arranged and configured to detect an intensity of the plurality of ultraviolets light-emitting diodes (LEDs) and a temperature sensor arranged and configured to measure a temperature of the dialysate.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
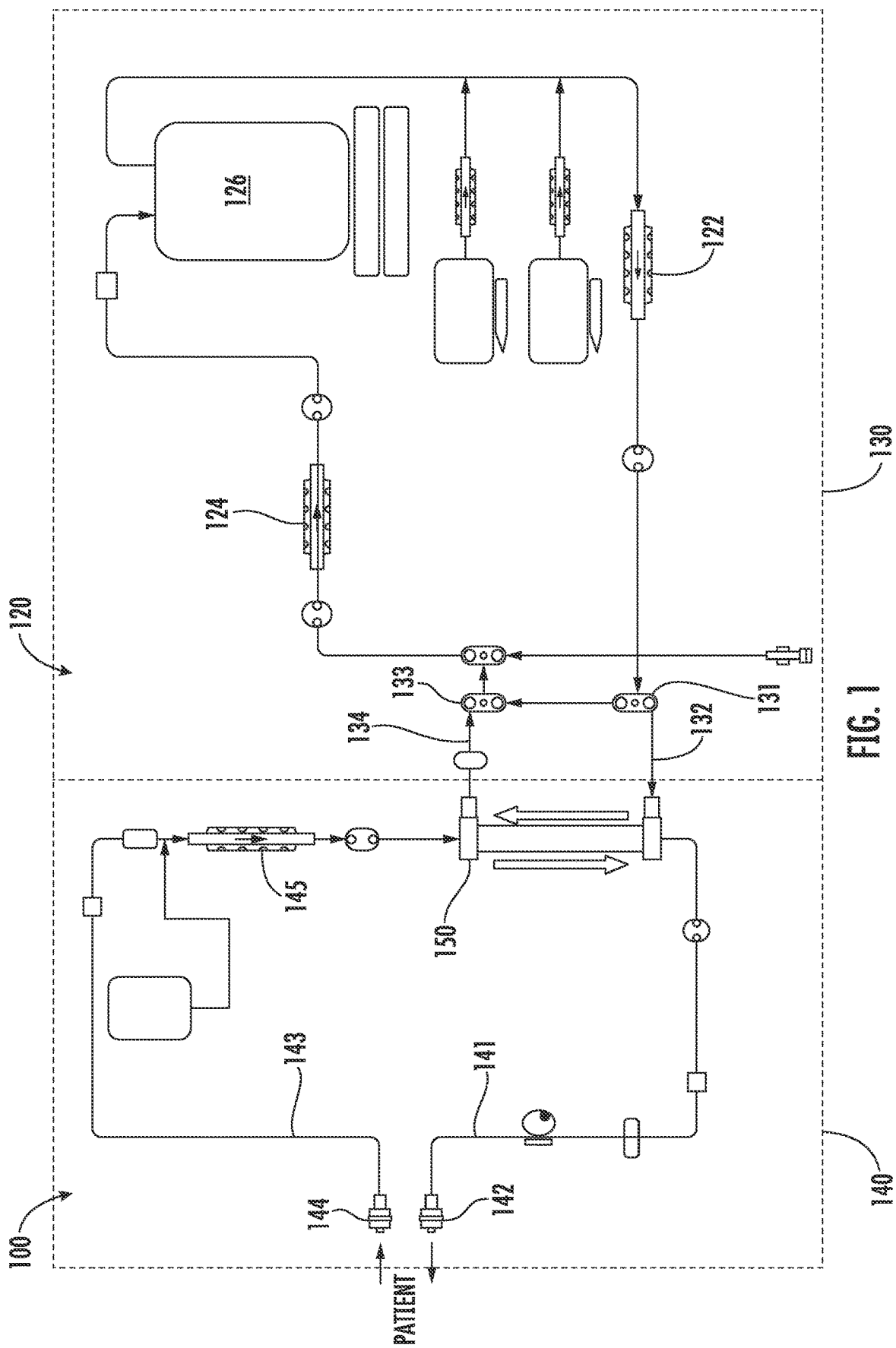
FIG. 1 illustrates an example of an embodiment of a hemodialysis system.

The present embodiments will now be described more fully hereinafter with reference to the accompanying drawings, in which several exemplary embodiments are shown. The subject matter of the present disclosure, however, may be embodied in many different forms and types of devices and systems for dialysis and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of an improved dialysis system (e.g., a hemodialysis system) and/or machine incorporating one or more ultraviolet chambers is disclosed herein. In accordance with one or more features of the present disclosure, the one or more ultraviolet chambers are arranged and configured to kill or deactivate reproductive systems of bacteria and viruses in the hemodialysis system during use. By incorporating one or more ultraviolet chambers and by placing the one or more ultraviolet chambers in different areas in the flow channel, path or circuit (terms used interchangeably herein without the intent to limit or distinguish) of the hemodialysis system, different benefits for improving patient safety and for streamlining clinic workflow between patients by preventing bacterial and viral contamination can be achieved. For example, in one embodiment, one or more ultraviolet chambers may be positioned immediately after the fluid path return or output from the dialyzer (e.g., immediately after the output of the dialyzer and prior to the input of the dialysis machine). Thus arranged, the ultraviolet chamber is arranged and configured to kill or deactivate bacteria and viruses in the spent dialysate prior to the spent dialysate entering the dialysis machine (e.g., hydraulics of the system). In addition, and/or alternatively, one or more ultraviolet chambers may be positioned immediately prior to the fluid path input to the dialyzer (e.g., immediately before the input of the dialyzer). Moreover, in one or more embodiments, one or more ultraviolet chambers may be positioned within other areas of the flow path. For example, one or more ultraviolet chambers may be positioned adjacent to secondary filters to prevent bacteria and virus from entering the hydraulic system and/or from entering into the patient. Thus arranged, by incorporating one or more ultraviolet chambers in strategic areas of the system, the ultraviolet chambers may eliminate, or at least greatly reduce, the possibility of contaminates in, for example, the dialysate, and thus eliminate the need for disinfection of the system between treatments. In addition, secondary benefits may also be achieved such as, for example, reducing the potential of chemical residual since utilization of chemical disinfection can be reduced or eliminated and stress reduction to hydraulic components, which in turn increases the life expectancy of the hydraulic components and decreases maintenance and/or cost since utilization of heat and/or chemical disinfection can be reduced.

While the present disclosure will be described and illustrated in connection with a particular hemodialysis system and/or machine, it should be appreciated that the present disclosure is not so limited and should not be limited to any particular type of dialysis machine or system. Rather, it is envisioned that the present disclosure and the one or more ultraviolet chambers may be used in connection with other types of dialysis machines or systems. For example, it is envisioned that one or more ultraviolet chambers may also be used in connection with peritoneal dialysis (PD) systems wherein, as will be appreciated by one of ordinary skill in the art, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Thus, the present disclosure should not be limited to any particular type of dialysis machine or system unless specifically claimed.

Referring to FIG. 1, an example embodiment of a hemodialysis system 100 is disclosed. As illustrated, in the example embodiment, the hemodialysis system 100 includes a dialysis machine 120 including a dialysate flow path 130, an extracorporeal blood flow path 140, and a dialyzer 150. In addition, the hemodialysis system 100 may include any number of additional components needed to manage, sense, etc. the flow of dialysate and/or blood through the hemodialysis system 100.

As will be readily appreciated by one of ordinary skill in the art, in use, the dialysis machine 120 and dialysate flow path 130 are arranged and configured to pump dialysate through the dialysate-side of the dialyzer 150. To this end, the dialysis machine 120 includes, inter alia, first and second dialysate pumps 122, 124 to circulate dialysate through the dialysate path 130. In use, the first and second pumps 122, 124 may move the dialysate through the flow path including into a dialysate reservoir 126, out of dialysate reservoir 126, and back through the dialyzer 150. As illustrated, the dialysate path 130 includes an outlet 132 to pump or move the dialysate through an outlet valve 131 and into the dialyzer 150 and an inlet 134 to receive spent dialysate through an inlet valve 133 from the dialyzer 150.

The extracorporeal blood path 140 includes a to-patient connector 142 at the end of a venous return line 141, a from-patient connector 144 at an end of an arterial line 143, and a blood pump 145 arranged and configured to pump or pull blood from the patient through the arterial line 143 through the blood side of the dialyzer 150 and back to the patient through the venous return line 142.

In use, the dialyzer 150 includes a cartridge comprising a semi-permeable membrane (e.g., a high flux membrane) arranged and configured to remove toxins from the blood. In one embodiment, the removal of toxins is accomplished by establishing a concentration gradient across the semi-permeable membrane by allowing the dialysate to flow on one side of the membrane in one direction while simultaneously allowing the blood to flow on the other side of the membrane in the opposite direction. The dialyzer 150 may be of any type suitable for hemodialysis, hemodiafiltration, hemofiltration, or hemoconcentration, as are known in the art. Examples of suitable dialyzers include, but are not limited to, Fresenius® F60, F80 available from Fresenius Medical Care of Lexington, Mass., Baxter Conn. 110, CT 190, Syntra® 160 available from Baxter of Deerfield, Ill., or Minntech Hemocor HPH® 1000, Primus® 1350, 2000 available from Minntech of Minneapolis, Minn.

It should be appreciated that while a particular embodiment of a dialysis machine including a dialysis path, an extracorporeal blood flow path, and a dialyzer have been described and illustrated, as previously mentioned, the concepts of the present disclosure may be used in connection with any dialysis or hemodialysis system now known or hereafter developed. As such, the present disclosure should not be limited to any particular dialysis or hemodialysis system unless specifically claimed.

In addition, since the configuration and operation of dialysis systems is well known to one of ordinary skill in the art, for the sake of brevity of the present disclosure, additional details on the configuration and operation of dialysis systems is omitted herefrom. For example, in one embodiment, additional details on the configuration and operation of dialysis systems can be found in U.S. patent application Ser. No. 16/521,193, filed on Jul. 24, 2019, entitled Method for Tailoring Dialysis Treatment Based on Sensed Potassium Concentrations in Blood Serum or Dialysate, the entire contents of which application is hereby incorporated in its entirety.

In accordance with one or more features of the present disclosure, the hemodialysis system 100 may include an ultraviolet chamber 200. In use, as will be described in greater detail below, the ultraviolet chamber 200 is arranged and configured to kill, deactivate, or at least greatly reduce, unwanted bacteria, viruses, or the like, that may be present in the dialysate. In accordance with one or more features of the present disclosure, by positioning, locating, etc. the ultraviolet chambers 200 in one or more locations within the flow path of the hemodialysis system, the ultraviolet chamber(s) can improve patient safety by eliminating, or at least greatly minimizing, the potential for bacterial and viral contamination. In addition, by preventing, or at least greatly reducing, the bacterial and viral contamination, the ultraviolet chamber(s) may streamline the clinic workflow between patients and enable the dialysis machine 120 to be cleaned simultaneously with the distribution of a dialysis treatment thereby eliminating, or at least greatly minimizing, post-operative cleanings.

Figure 2:
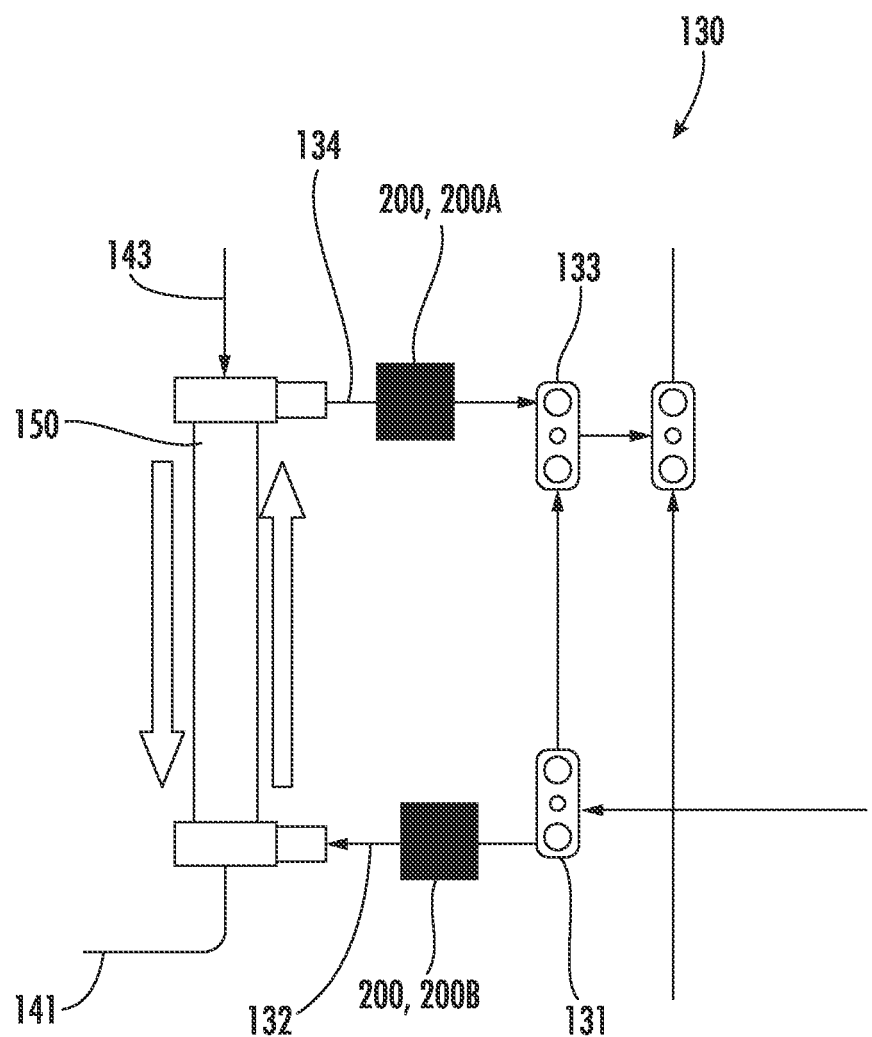
FIG. 2 illustrates a detailed view of a portion of the hemodialysis system shown in FIG. 1, the hemodialysis system incorporating one or more ultraviolet chambers in accordance with one or more features of the present disclosure.

Referring to FIG. 2, in one embodiment, an ultraviolet chamber 200 may be positioned within the dialysate flow path 130. More specifically, a first ultraviolet chamber 200A may be positioned within the dialysate flow path 130 immediately after, adjacent to, or between, the outlet of the dialyzer 150 and the inlet 134 (e.g., valve 133) of the dialysate path 130. Thus arranged, the ultraviolet chamber 200 is arranged and configured to receive and clean the spent dialysate exiting the dialyzer 150 prior to entering any portion of the dialysis machine 120 thereby ensuring that the dialysis machine 120 does not come into contact with any contaminated dialysate (e.g., positioning the ultraviolet chamber 200 in the fluid path return (e.g., inlet 134) to the dialysis machine 120 from the dialyzer 150 will prevent bacteria and viruses from getting into the hydraulic of the systems. That is, bacteria and/or virus is prevented from entering the hydraulics of the dialysis machine). Alternatively, the ultraviolet chamber 200 may be positioned within or inside of the dialysis machine such as, for example, where the spent dialysate enters the dialysis machine.

In addition, and/or alternatively, as illustrated, a second ultraviolet chamber 200B may be positioned within the dialysate flow path 130. More specifically, a second ultraviolet chamber 200B may be positioned within the dialysate flow path 130 immediately before, adjacent to, or between, the inlet of the dialyzer 150 and the outlet 132 (e.g., valve 131) of the dialysate path 130. Thus arranged, the second ultraviolet chamber 200B is arranged and configured to receive and clean the dialysate exiting the dialysis machine 120 prior to entering the dialyzer 150 to kill, deactivate, or at least greatly reduce, any bacteria or viruses that may be present in the dialysate prior to any interaction with the patient's blood in the dialyzer 150 (e.g., positioning the ultraviolet chamber 200 in the fluid path after exiting the dialysis machine 120 but prior to entering the dialyzer 150 provides additional, secondary protection to the patient by ensuring any bacteria or virus is killed prior to interacting with the patient's blood in the dialyzer 150). Alternatively, the ultraviolet chamber 200 may be positioned within or inside of the dialysis machine.

Figure 3:
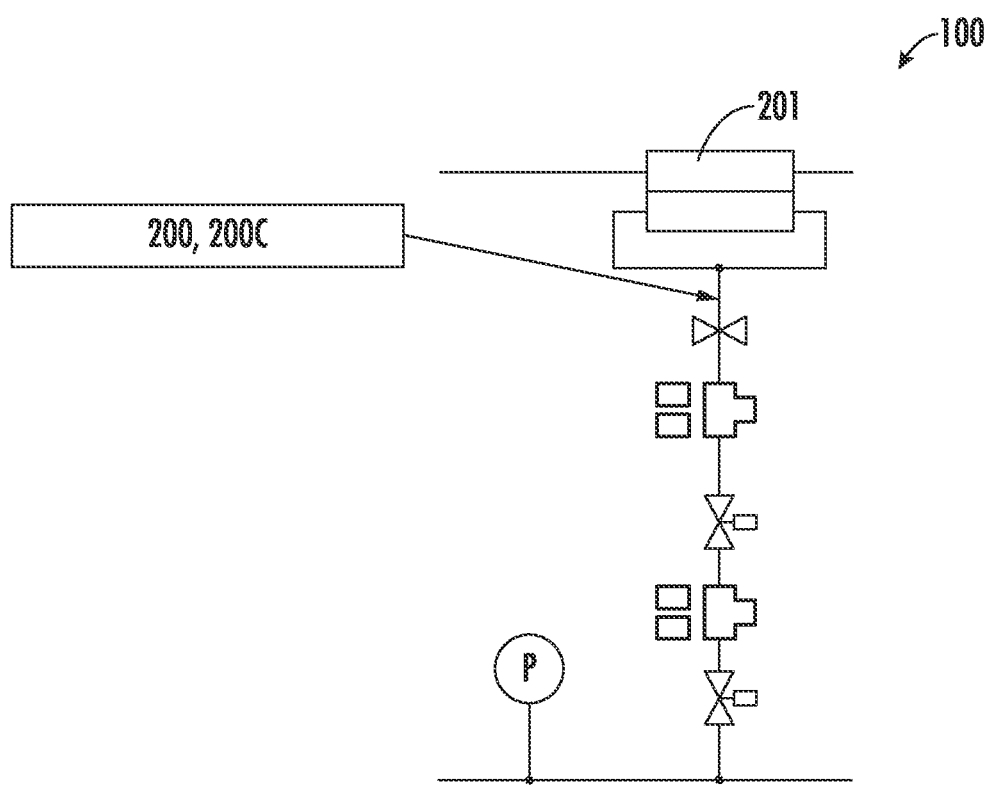
FIG. 3 illustrates a detailed view of a portion of an alternate hemodialysis system, the hemodialysis system incorporating one or more ultraviolet chambers in accordance with one or more features of the present disclosure.

In addition, and/or alternatively, the hemodialysis system 100 may include one or more ultraviolet chambers 200 strategically positioned within the fluid flow path. For example, with reference to FIG. 3, in alternate embodiments of hemodialysis systems, the hemodialysis system may include a substitution fluid path. In use, the dialysis machine may be used to pump ultra-clean fluid into the patient to aid in additional treatments. In such embodiments, in accordance with one or more features of the present disclosure, an ultraviolent chamber 200C may be positioned within the substitution fluid path to ensure any bacteria or viruses in the substitution fluid path are killed, or at least greatly reduced, prior to being injected within the patient. As illustrated, in one embodiment, the substitution fluid path may include a dialysate filter 201. The ultraviolet chamber 200C may be positioned adjacent to the dialysate filter 201 in the substitution fluid path.

In accordance with one or more features of the present disclosure, by incorporating one or more ultraviolet chambers 200 into the fluid flow paths of a hemodialysis system, a number of advantages are achieved. For example, patient safety and comfort are improved. Utilization of one or more ultraviolet chambers 200 in the flow path of the hemodialysis system kills, or at least greatly reduces the likelihood that a patient's blood will come into contact with one or more bacteria or viruses, thus improving patient safety and providing comfort to patients who may feel nervous about their safety when sharing dialysis machines during growing concerns in disease transmission. In addition, incorporating one or more ultraviolet chambers 200 into the fluid flow paths of a hemodialysis system streamlines clinic workflow between patients by preventing bacterial and viral contamination of the hydraulics of the system and thus eliminates the need to disinfect the dialysis machine between treatments. As a result, the dialysis machines may be immediately used to treat subsequent patients thereby reducing downtime (e.g., ultraviolet chambers 200 provide expedited cleaning procedures after patient use, which can reduce cost and eliminate the need for disinfection between treatments). In addition, this provides other secondary benefits including eliminating, or at least reducing, the chances of chemical residual since utilization of chemical disinfection will be eliminated or at least reduced. In addition, since heat and/or chemical disinfection will be reduced, there will be less stress to hydraulic components, which in turn will increase the service life of the hydraulic components thereby reducing maintenance and/or cost.

In accordance with one or more features of the present disclosure, the one or more ultraviolet chambers 200 may have any suitable shape and/or configuration now known or hereafter developed. As previously mentioned, in use, by passing fluid (e.g., dialysate) through the ultraviolet chambers 200, bacteria and viruses may be killed, deactivated, or at least greatly reduced. For example, use of ultraviolet exposure has been found to kill influenza, hepatitis B, tuberculosis, salmonella, cholerae, echovirus, bacillus, coxsackie, etc. In use, the exposure time for each bacteria or virus may vary depending on intensity and exposure time. For example, it has been found that most bacteria and virus may be killed by exposing the fluid to ultraviolet light between 0.1 seconds to 0.8 seconds. As will be appreciated by one of ordinary skill in the art, the required exposure time may be dependent upon a number of variables including ultraviolet ("UV") intensity, UV wavelength, distance from the UV source, etc. For example, in one embodiment, it has been discovered that the Hepatitis B virus will be inactivated by exposure to UVC radiation at a dosage of 30,000 µwatt·sec/cm2 in 0.73 sec. As such, by subjecting the dialysate fluid to an ultraviolet light that satisfy these requirements, the current cleaning procedures (e.g., current heating and/or chemical disinfection) can be eliminated. Thus, after a Hepatitis B patient has completed his/her dialysis treatment, since the Hepatitis B virus is killed or deactivated during the treatment in the hydraulic, the dialysis machine can be reused without undergoing additional cleaning thus enabling clinics to expedited cleaning procedures after patients, which can reduce costs.

Figure 4:
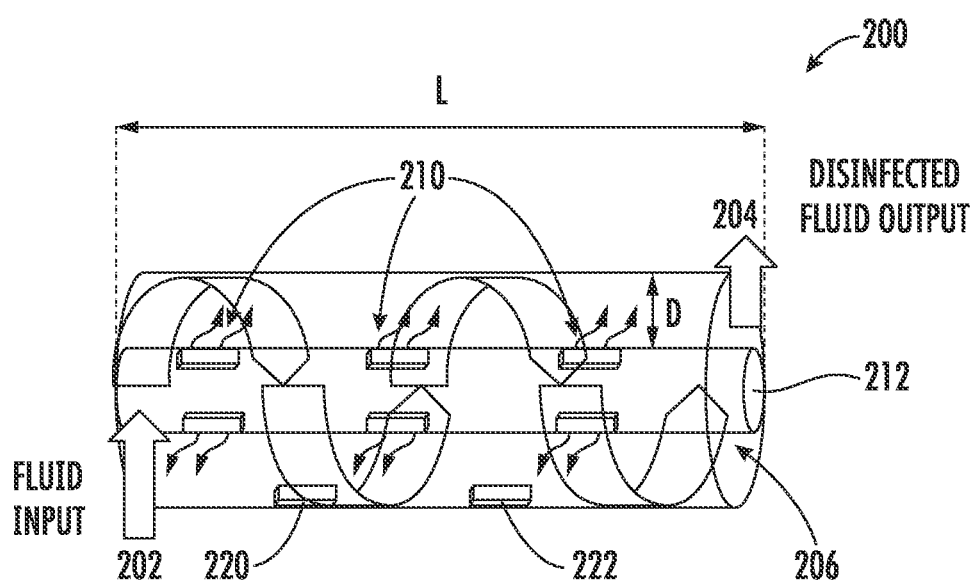
FIG. 4 illustrates a cross-section view of an example embodiment of an ultraviolet chamber that may be used in the hemodialysis system of FIGS. 2 and 3 in accordance with one or more features of the present disclosure.

Referring to FIG. 4, in accordance with one or more features of the present disclosure, an example embodiment of an ultraviolet chamber 200 that may be used is illustrated. As illustrated, the ultraviolet chamber 200 may include an inlet 202 for receiving fluid, an outlet 204 for exiting fluid, and a fluid flow path 206 extending between the inlet 202 and the outlet 204. In one embodiment, as illustrated, the ultraviolet chamber 200 may include a cylindrical shape, although this is but one configuration and other shapes are envisioned. In addition, as illustrated, the ultraviolet chamber 200 may include a plurality of ultraviolets light-emitting diodes (LEDs) 210 arranged and configured to provide the ultraviolet light. In one embodiment, the ultraviolet LEDs 210 may provide ultraviolet light with a wavelength of 254 nm, although other configurations are envisioned. In one embodiment, as illustrated, the ultraviolet chamber 200 may include an internal chamber 212 (e.g., internal cylindrical chamber extending between the ends of the chamber 200) for housing or enclosing the ultraviolet LEDs 210 so that the ultraviolet LEDs 210 are kept separated from the fluid (e.g., sealed from the fluid flow path 206). In order to achieve the needed intensity, the ultraviolet chamber 200 may include a length L. In addition, the distance of the LEDs 210 from the outer surface of fluid flow path 206 may be a distance D.

In one embodiment, to ensure proper intensity, the distance D may be minimized as it has been found that the smaller the distance D, the greater the intensity. In addition, in order to reduce the length L of the ultraviolet chamber 200, in one embodiment, the fluid flow path 206 is arranged and configured so that the entering fluid spirals about the fluid flow path 206 around the internal chamber 212. This is in contrast to moving straight across from the inlet 202 to the outlet 204. By arranging the fluid flow path 206 so that the entering fluid must spiral about the internal chamber 212, the effective length of travel, and thus the exposure time, of the fluid is increased thereby enabling the overall length L of the ultraviolet chamber 200 to be reduced.

In addition, in one embodiment, as illustrated, the ultraviolet chamber 200 may include one or more photodetector sensors 220 arranged and configured to detect intensity of the ultraviolet LEDs 210. In this manner, the photodetector sensors 220 can monitor the ON/OFF status of the ultraviolet LEDs 210. In addition, and/or alternatively, the ultraviolet chamber 200 may include one or more temperature sensors 222 arranged and configured to measure a temperature of the dialysate.

The ultraviolet chambers described herein has been explained in connection with dialysis machines and/or systems having a particular configuration. It is contemplated that the ultraviolet chambers described herein may be used with dialysis machines and/or systems having other configurations, for example, different types of dialysis machines. The ultraviolet chambers described herein may be used with any appropriate dialysis machine and/or system.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. In addition, while certain embodiments have been described and illustrated with certain features, it is envisioned that features of one embodiment may be used in combination with other embodiments. Moreover, the following claims are hereby incorporated into this Detailed Description by this reference, with each claim standing on its own as a separate embodiment of the present disclosure.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A hemodialysis system comprising:
a dialyzer arranged and configured to filter a patient's blood;
a hemodialysis machine arranged and configured to move dialysate through the dialyzer, the hemodialysis machine including an outlet valve and an outlet fluid flow path to move dialysate from the hemodialysis machine to the dialyzer, and an inlet valve and an inlet fluid flow path to receive dialysate from the dialyzer; and
one or more ultraviolet chambers arranged and configured to kill bacteria, viruses, or a combination thereof, wherein the one or more ultraviolet chambers include a first ultraviolet chamber positioned in the inlet fluid flow path between the dialyzer and the inlet valve to kill any bacteria, viruses, or combination thereof in the dialysate prior to the dialysate entering the hemodialysis machine;
wherein each of the one or more ultraviolet chambers include a cylindrical body including:
a first end;
a second end;
an inlet positioned adjacent the first end for receiving dialysate;
an outlet positioned adjacent the second end for exiting dialysate;
an internal chamber extending between the first and second ends, the internal chamber including a plurality of ultraviolet light-emitting diodes (LEDs) arranged and configured to emit ultraviolet light; and
an internal fluid flow path extending between the cylindrical body and the internal chamber and extending between the inlet and the outlet, wherein the fluid flow path moves the dialysate through a spiral trajectory about the internal chamber.

2. The hemodialysis system of claim 1, wherein the one or more ultraviolet chambers eliminate a need for disinfecting the hemodialysis machine between patients.

3. The hemodialysis system of claim 1, wherein the one or more ultraviolet chambers further comprises a second ultraviolet chamber positioned in the outlet fluid flow path between the outlet valve and the dialyzer to kill any bacteria, viruses, or combination thereof in the dialysate prior to entering the dialyzer to kill any bacteria, viruses, or combination thereof, prior to interacting with the patient's blood in the dialyzer.

4. The hemodialysis system of claim 1, wherein the one or more ultraviolet chambers further comprises a third ultraviolet chamber positioned within a substitution fluid path arranged and configured to pump a fluid into a patient's body.

5. The hemodialysis system of claim 1, wherein the dialyzer is arranged and configured to receive and pass therethrough the patient's blood.

6. The hemodialysis system of claim 1, wherein each of the one or more ultraviolet chambers include a photodetector sensor arranged and configured to detect an intensity of the plurality of ultraviolet light-emitting diodes (LEDs) and a temperature sensor arranged and configured to measure a temperature of the dialysate.

7. A hemodialysis system comprising:
a dialyzer arranged and configured to filter a patient's blood;
a hemodialysis machine arranged and configured to move dialysate through the dialyzer, the hemodialysis machine including an outlet valve and an outlet fluid flow path to move dialysate from the hemodialysis machine to the dialyzer, and an inlet valve and an inlet fluid flow path to receive dialysate from the dialyzer; and
one or more ultraviolet chambers arranged and configured to kill bacteria, viruses, or a combination thereof, wherein the one or more ultraviolet chambers include:
a first ultraviolet chamber positioned in the inlet fluid flow path between the dialyzer and the inlet valve to kill any bacteria, viruses, or combination thereof in the dialysate prior to the dialysate entering the hemodialysis machine; and
a second ultraviolet chamber positioned in the outlet fluid flow path between the outlet valve and the dialyzer to kill any bacteria, viruses, or combination thereof in the dialysate prior to entering the dialyzer to kill any bacteria, viruses, or combination thereof, prior to interacting with the patient's blood in the dialyzer;
wherein each of the one or more ultraviolet chambers include a cylindrical body including:
a first end;
a second end;
an inlet positioned adjacent the first end for receiving dialysate;
an outlet positioned adjacent the second end for exiting dialysate;
an internal chamber extending between the first and second ends, the internal chamber including a plurality of ultraviolet light-emitting diodes (LEDs) arranged and configured to emit ultraviolet light; and
an internal fluid flow path extending between the cylindrical body and the internal chamber and extending between the inlet and the outlet, wherein the fluid flow path moves the dialysate through a spiral trajectory about the internal chamber.

8. The hemodialysis system of claim 7, wherein the one or more ultraviolet chambers eliminate a need for disinfecting the hemodialysis machine between patients.

9. The hemodialysis system of claim 7, wherein each of the one or more ultraviolet chambers include a photodetector sensor arranged and configured to detect an intensity of the plurality of ultraviolet light-emitting diodes (LEDs) and a temperature sensor arranged and configured to measure a temperature of the dialysate.

10. An ultraviolet chamber arranged and configured to be used in a hemodialysis system, the ultraviolet chamber comprising:
a cylindrical body including:
a first end;
a second end;
an inlet positioned adjacent the first end for receiving dialysate;
an outlet positioned adjacent the second end for exiting dialysate;
an internal chamber extending between the first and second ends, the internal chamber including a plurality of ultraviolet light-emitting diodes (LEDs) arranged and configured to emit ultraviolet light; and
an internal fluid flow path extending between the cylindrical body and the internal chamber and extending between the inlet and the outlet, wherein the fluid flow path is arranged and configured to move the dialysate through a spiral trajectory about the internal chamber.

11. The ultraviolet chamber of claim 10, further comprising a photodetector sensor arranged and configured to detect an intensity of the plurality of ultraviolet light-emitting diodes (LEDs) and a temperature sensor arranged and configured to measure a temperature of the dialysate.

* * * * *